(12) United States Patent
Najar

(10) Patent No.: US 9,282,959 B2
(45) Date of Patent: Mar. 15, 2016

(54) LAPAROSCOPIC INSTRUMENT

(75) Inventor: Azad Najar, Vasteras (SE)

(73) Assignee: LAPROTECH AB, Vasteras (SE)

( * ) Notice: Subject to any disclaimer, the term of this patent is extended or adjusted under 35 U.S.C. 154(b) by 374 days.

(21) Appl. No.: 13/808,737

(22) PCT Filed: Jul. 4, 2011

(86) PCT No.: PCT/SE2011/050902
§ 371 (c)(1),
(2), (4) Date: Mar. 29, 2013

(87) PCT Pub. No.: WO2012/005671
PCT Pub. Date: Jan. 12, 2012

(65) Prior Publication Data
US 2013/0184721 A1    Jul. 18, 2013

(30) Foreign Application Priority Data

Jul. 5, 2010  (SE) ...................................... 1050737

(51) Int. Cl.
*A61B 17/04*        (2006.01)
(52) U.S. Cl.
CPC ......... *A61B 17/0469* (2013.01); *A61B 17/0487* (2013.01); *A61B 2017/0488* (2013.01)
(58) Field of Classification Search
CPC .................. A61B 17/0401; A61B 2017/0454; A61B 17/0469; A61B 17/0487; A61B 2017/0488; A61B 2017/0409; D04D 1/04
USPC ......... 606/148, 142, 143, 219, 139, 145, 232, 606/147; 227/175.1–175.4; 132/200; 223/48
See application file for complete search history.

(56) References Cited

U.S. PATENT DOCUMENTS

| 5,456,271 A * | 10/1995 | Legette .......................... 132/212 |
| 5,709,694 A | 1/1998 | Greenberg et al. |
| 5,817,107 A | 10/1998 | Schaller |
| 5,957,936 A | 9/1999 | Yoon et al. |
| 5,984,932 A | 11/1999 | Yoon |

(Continued)

FOREIGN PATENT DOCUMENTS

| EP | 1952770 | 8/2008 |
| EP | 2098176 | 9/2009 |

(Continued)

OTHER PUBLICATIONS

International Search Report dated Oct. 25, 2011, corresponding to PCT/SE2011/050902.

(Continued)

*Primary Examiner* — Todd E Manahan
*Assistant Examiner* — Majid Jamialahmadi
(74) *Attorney, Agent, or Firm* — Young & Thompson

(57) ABSTRACT

A laparoscopic instrument includes a handle unit by which a user may hold the instrument, an elongated first tube attached to the handle unit, a second tube arranged slidable in relation to the first tube, that the second tube is provided with a thread gripping member capable of gripping suture threads, a locking member arranged to the tubes such that, when the second tube is moved in relation to the first tube, gripped suture threads are locked. The invention is characterized in that the device further includes storage elements for a number of rings, and a ring feeding member capable of, upon activation, moving the ring from the storage elements to a free position in which the suture threads run through the ring.

8 Claims, 5 Drawing Sheets

(56) References Cited

U.S. PATENT DOCUMENTS

| | | | |
|---|---|---|---|
| 6,022,360 A | 2/2000 | Reimels et al. | |
| 6,086,608 A | 7/2000 | Ek et al. | |
| 6,159,224 A | 12/2000 | Yoon | |
| 6,165,204 A | 12/2000 | Levinson et al. | |
| 2004/0216758 A1* | 11/2004 | Rascoe | 132/200 |
| 2005/0076931 A1* | 4/2005 | Leung et al. | 132/200 |
| 2009/0223028 A1 | 9/2009 | Cui et al. | |
| 2010/0010511 A1* | 1/2010 | Harris et al. | 606/143 |
| 2010/0203276 A1* | 8/2010 | Wasserman et al. | 428/36.9 |
| 2013/0282028 A1* | 10/2013 | Conklin et al. | 606/144 |

FOREIGN PATENT DOCUMENTS

| | | |
|---|---|---|
| WO | 98-48701 | 11/1998 |
| WO | 2007-073343 | 6/2007 |

OTHER PUBLICATIONS

Extended European search report, dated Jul. 23, 2015, in corresponding European Patent Application No. 11803902.3.

* cited by examiner

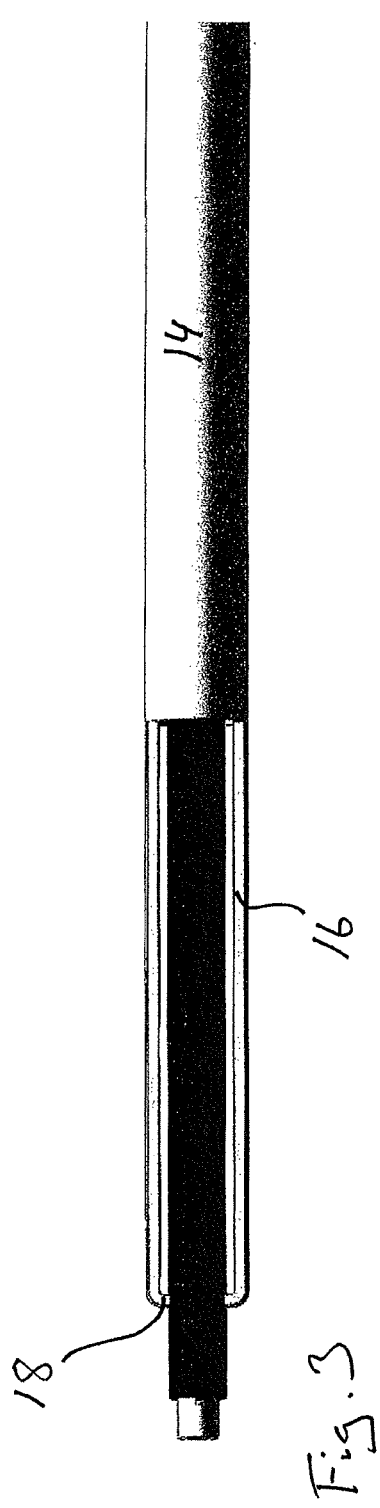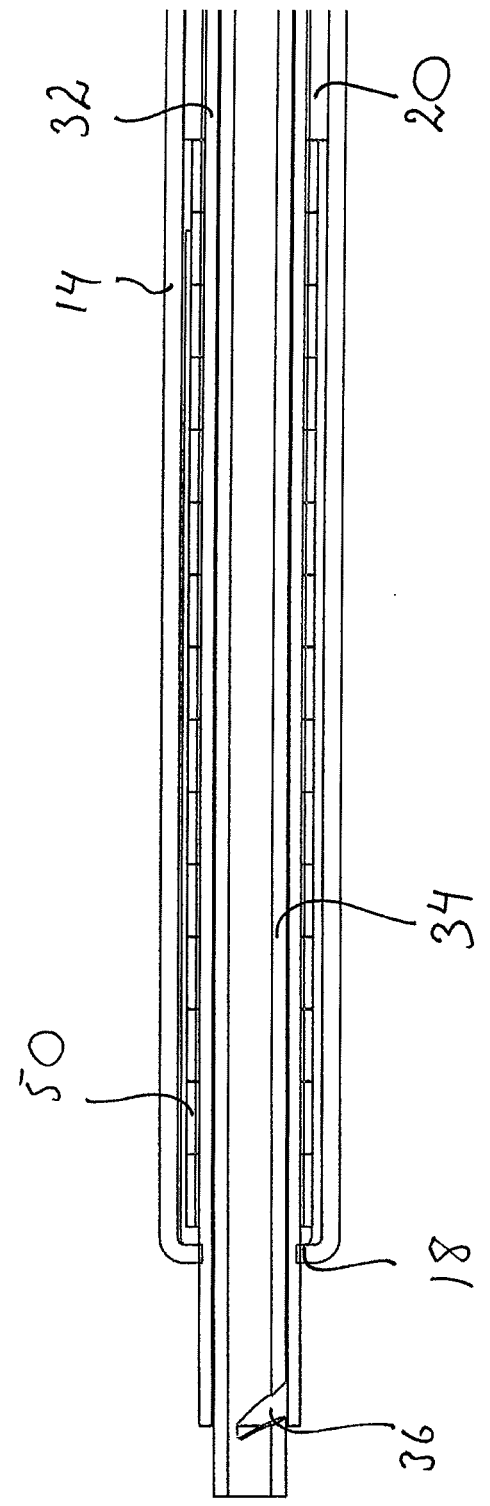

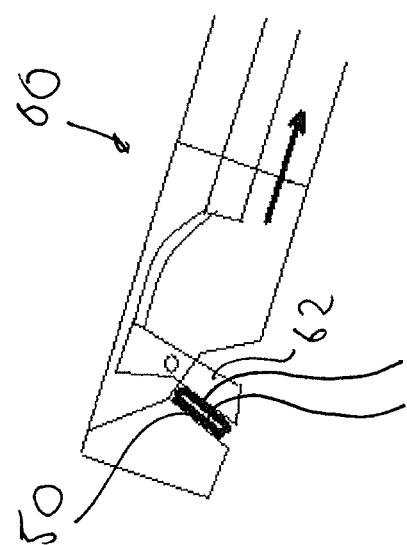
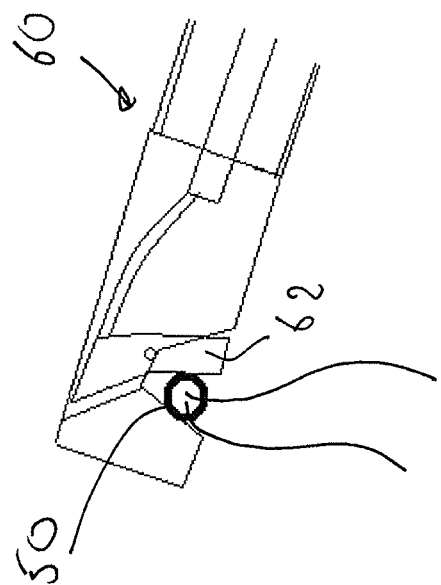

US 9,282,959 B2

LAPAROSCOPIC INSTRUMENT

TECHNICAL AREA

The present invention relates to a laparoscopic instrument and in particular an instrument that facilitates the knotting of stitches in the interior of a patient.

BACKGROUND OF INVENTION

During a laparoscopic operation instruments with long handles are used in order to perform all steps of the operation. As a summary, the most important sewing-steps in a laparoscopic operation are the following: a first instrument holds the needle. The needle and the hanging thread are on one side of the tissues. With the help of the first instrument the needle is guided through the tissues that are to be sewn together. A second instrument receives the needle and then the first instrument releases the needle. The second instrument pulls the needle through the tissues so that the needle goes through from one side to a second side. The second instrument releases the needle and instead grips the thread at a suitable distance from the tissue on the second side. With suitable movements the thread is twisted around the first instrument. Then the first instrument grips the thread on the first side of the tissue. The first instrument pulls the end of the thread back so that a knot is created. Both instruments are pulled so that the tissues are brought together. A similar process is repeated two or more times so that at least three knots on each other are obtained so that the risk of them loosing the grip is minimized.

As understood from the above description, to make a knot during a laparoscopic operation is one of the most time-consuming parts of the operation. Limited possibilities of movement, two-dimensional viewing via a TV screen and the long handle in the instrument are some important factors that contribute to a higher degree of complexity. It is often that a knot may take more than ten minutes and the surgeon has to try several times before succeeding. Longer operation time is a large load for both the patient and the surgeon.

The applicant of the present invention has therefore developed a number of laparoscopic instruments that greatly facilitates a laparoscopic operation and thus shortens the operation time. These instruments are disclosed in the patent application, publication no. WO2007/073343. With the aid of these instruments both the entering of the thread through the tissues as well as the following knotting are handled much more easily than before. There is also described a method and a device where the ends of the thread through the tissue are brought together not by a knot but by a metal clip which is pressed by the device to secure the threads.

However, even if the step of bringing the ends of the thread together with the above mentioned instruments has been reduced compared to before, there is still room for improvements in this area.

BRIEF DESCRIPTION OF INVENTION

A main object of the present invention is to provide a laparoscopic instrument that will further facilitate and shorten the operation time and in particular the step of bringing the threads together.

This object is obtained by a laparoscopic instrument according to the features of the independent patent claim. Preferable embodiments of the present invention form the subject of the dependent patent claims.

According to a main aspect of the invention it is characterised by a laparoscopic instrument comprising a handle unit by which a user may hold the instrument, an elongated first tube attached to said handle unit, a second tube arranged slidable in relation to said first tube, that said second tube is provided with a thread gripping member capable of gripping suture threads, a locking member arranged to said tubes such that, when said second tube is moved in relation to said first tube, gripped suture threads are locked, characterised in that the device further comprises storage means for a number of ring, and a ring feeding member capable of, upon activation, moving said ring from said storage means to a free position in which said suture threads run through said ring.

According to another aspect of the invention, it comprises a lever member arranged adjacent to said handle and operationally connected to said second tube for enabling movement in relation to said first tube.

According to yet another aspect of the invention, said storage means comprises the outer surface of said second tube, on which the ring are releasibly positioned.

According to a further aspect of the invention, said ring feeding member comprises a third tube arranged outside said second tube.

According to yet a further aspect of the invention, said ring feeding member further comprises a rotational member threadedly arranged to said housing and connected to said third tube such that rotation causes said third tube to be moved in the proximal direction, releasing a ring.

According to another aspect of the invention, it comprises a fourth tube arranged outside said third tube for protecting said ring.

According to a further aspect of the invention, the proximal end of said fourth tube is arranged with flexible arms having inwardly directed ledges at their proximal ends for releasibly holding said ring.

There are a number of advantages with the present invention. B utilizing at least one tube in which a gripping member is slidably arranged, a very fast and accurate gripping of the suture threads is ascertained. Further since the ring are readily available from a storage means on the instrument, it is easy to place the ring in relation to the suture threads for joining them by the ring.

A further advantage is to have further tubes surrounding the gripping and locking tubes, which operate and move the rings when they are to be used by sliding movement, which sliding movement can be provided by a threaded rotational member. preferably the suture thread runs through the instrument and cooperates with a needle laparoscopic instrument, whereby one part of the thread is already present in the instrument before a stitch and whereby the other end of the thread is easily gripped by the instrument for the subsequent joining of the threads for performing a stitch. In all a very versatile and time-saving instrument is obtained.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 2 shows a cross-sectional side view of a proximal part of the instrument according to the present invention, FIG. 3 shows a side view of the proximal part of the instrument, FIG. 6 shows the principle of squeezing ring that are used with the present invention.

DETAILED DESCRIPTION OF THE INVENTION

Figure 1:
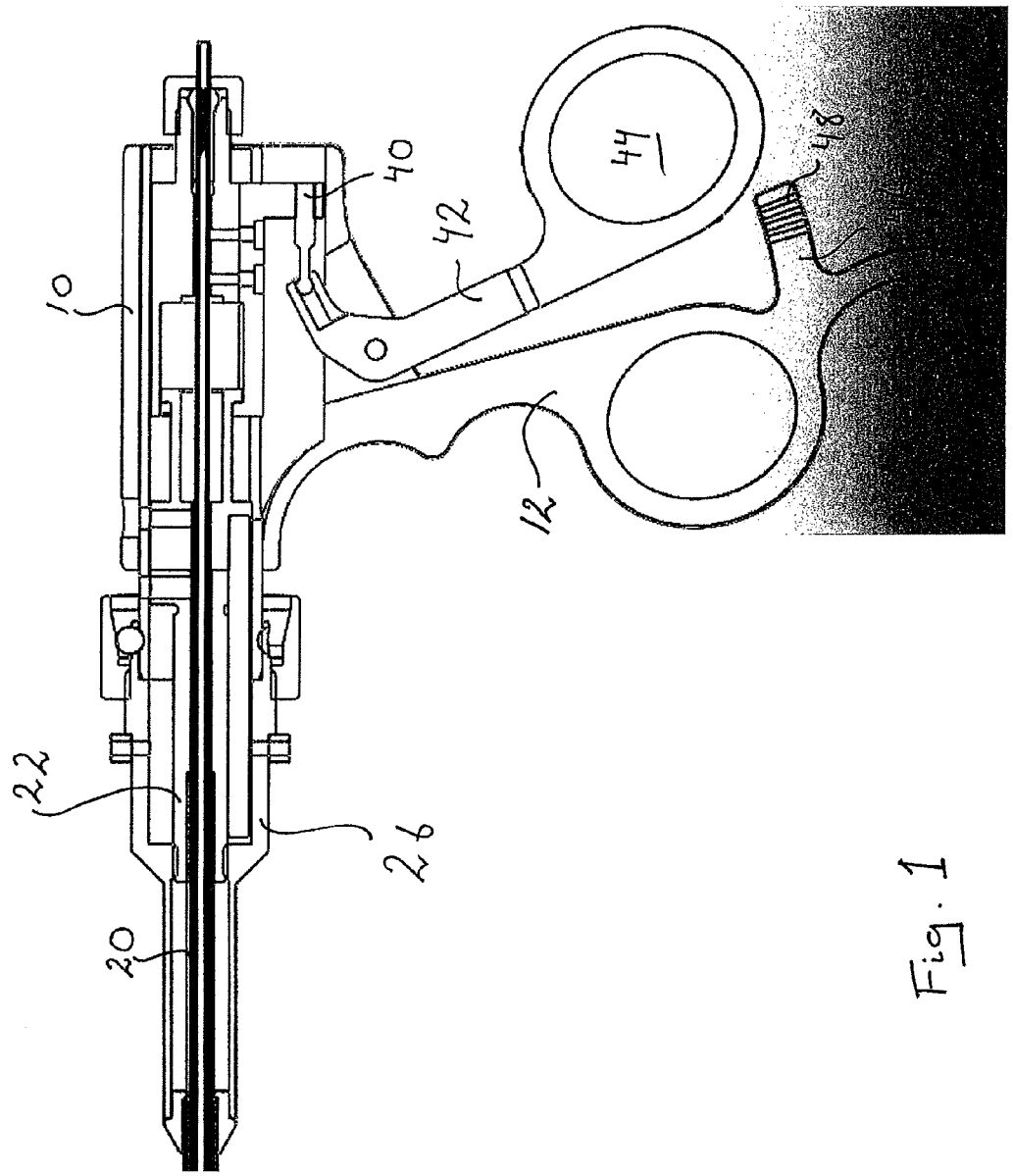
FIG. 1 shows a cross-sectional side view of a distal part of the instrument according to the present invention.
Figure 4:
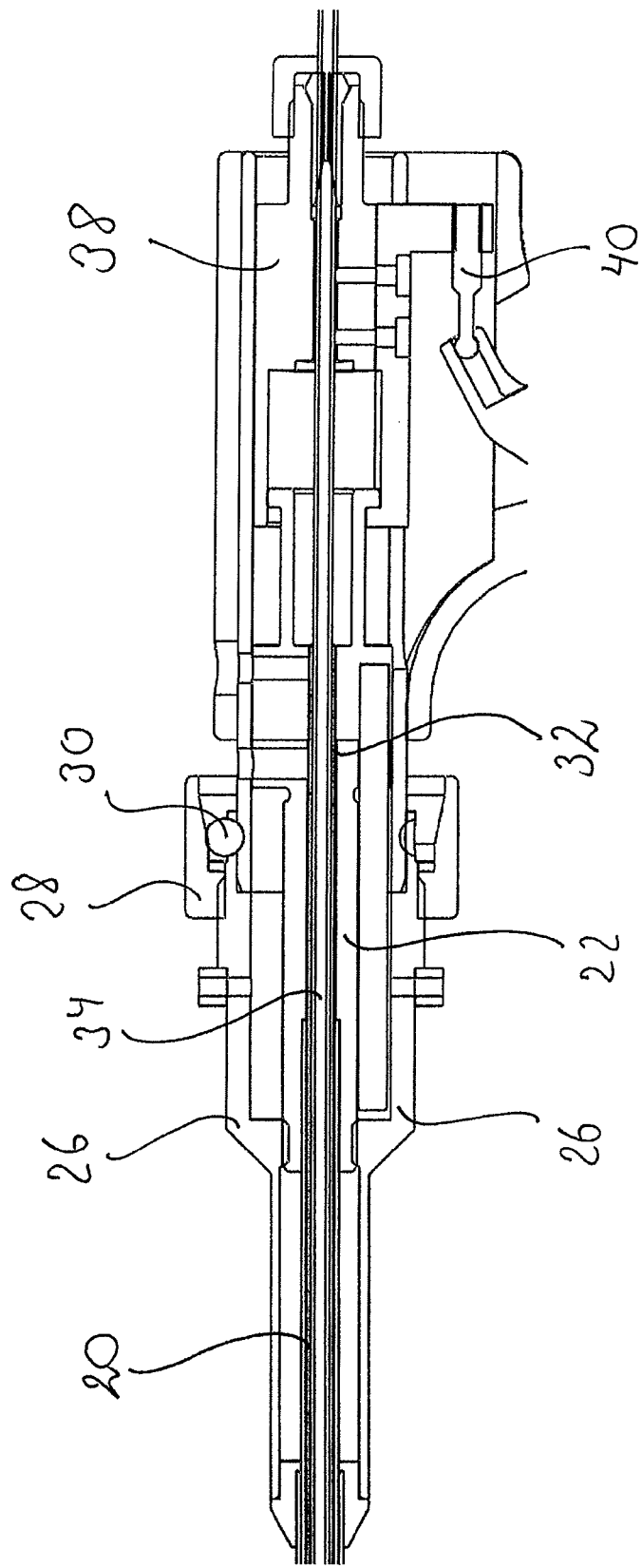
FIG. 4 shows a detailed cross-sectional view of the instrument.

In the present application, when the term "distal part/end" is used, this refers to the part/end of the device, or the parts/ends of the members thereof, which is/are located the furthest away from the patient when in use. Correspondingly, when the term "proximal part/end" is used, this refers to the part/end of the device, or the parts/ends of the members thereof, which, is/are located closest to, or inside, the patient during use.

The instrument shown in the drawings comprises a generally tubular housing 10. A handle 12 is attached to the outer surface of the housing and shaped as to provide a grip for a user. At a proximal end of the housing a first tube 14, hereafter named guide tube, is attached. The proximal end of the guide tube 14 is arranged with longitudinally extending slits, forming arms 16 between the slits, FIG. 3, which arms are resilient in the radial direction. At the proximal end of the arms 16 inwardly directed ledges 18 are arranged. The function of the arms 16 will be described below.

Figure 5:
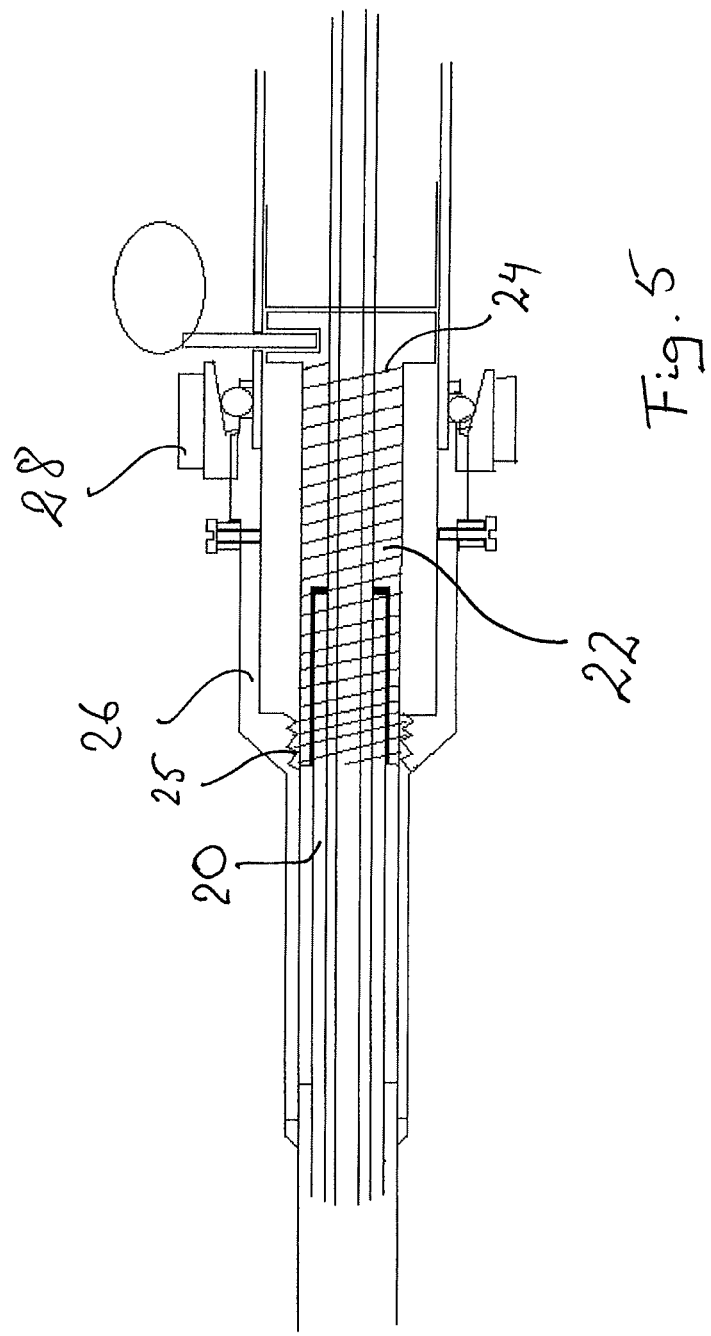
FIG. 5 shows another detailed cross-sectional view of the instrument.

Inside the guide tube 14 a second tube 20 is arranged, hereafter named feed tube, is slidably arranged. The distal end of the feed tube is attached to a support 22, which support is arranged with threads 24 on its outer surface, FIG. 5. These threads cooperate with threads 25 on a generally cylindrical feed member 26 arranged rotatable at the proximal end of the housing. A feed nut 28 is attached to the feed member 26 and supported to the housing via bearings 30. The feed nut 28 may be rotated by a user such that when said feed nut 28 and thus said feed member 26 are rotated, the feed tube 20 is moved in the proximal direction of the device.

Inside the feed tube 20 a third tube 32 is arranged, hereafter named shuttle tube, which shuttle tube 32 is attached to the housing of the device. Inside the shuttle tube a fourth tube 34, hereafter named thread locking tube, is arranged slidable in relation to the shuttle tube 32. The proximal end of the thread locking tube 34 is arranged with an inwardly directed notch 36, FIG. 2. The distal end of the thread locking tube 34 is attached to a post 38 inside the housing, which post is arranged slidable. The post is provided with a pivot 40. A lever 42 is pivotally arranged to the housing adjacent the handle and having an upper end attached to the pivot 40 of the post 38. The lower end of the lever is designed with a circle 44 in which a finger of a user may fit, such as the thumb. The handle 12 is further arranged with a distally directed arm 46, having notches 48 on a side surface, which notches 48 are arranged to cooperate with corresponding notches on an opposite side surface of the lever 42, thereby providing a relasible locking function of the lever 42 in relation to the handle 12. Further, the distal end of the device is preferably arranged with a reel (not shown), on which suture thread is wound. The thread is arranged through the thread locking tube 34 from the distal end to the proximal end.

The device is intended to function as follows. Beforehand a number of clips 50, of any suitable material, having a general ring-shape, have been pushed onto the shuttle tube 32 from the proximal end of the device, FIG. 2, past the inwardly directed ledges 18 of the arms 16 of the guide tube 14. The end of the thread at the proximal end of the device is during use connected to a needle of another laparoscopic instrument and is pushed through the tissue to be sewn together. Then the free end of the thread is put around the notch 36 of the thread locking tube 34. Then the lever 42 is pushed in the proximal direction towards the handle 12. This causes the post 38, pivotally connected to the upper end of the lever 42, to be pushed in the distal direction, as well as the thread locking tube 34 since it is attached to the post. This in turn causes the proximal end of the thread locking tube 34, together with the threads to be pulled inside shuttle tube 32, thereby locking the threads. The lever 42 is now releasibly locked to the handle 12 and the grip of the handle may now be removed. Instead, the user now grips the knob 28 and turns it in relation to the housing. The rotation then causes the feed tube 20 to be moved in the proximal direction due to the threaded connection between the feed member 26 and the support of the feed tube 20. The movement of the feed tube 20 causes the rings 50 to be pushed in the proximal direction until the most proximal ring 50 is pushed past the ledges 18 of the resilient arms o the outer tube. The ring 50 now is free with the threads through it, FIG. 6a. Now a suitable instrument 60 containing a pair of pliers 62 is introduced by which the ring 50 may be moved to an appropriate position along the threads and is deformed by the pair of pliers to squeeze the threads, FIG. 6b, whereby the stitch is finished. The thread is cut and a subsequent stitch may be performed as described above.

It is to be understood that the embodiment described above and shown in the drawings is to be regarded only as a non-limiting example of the invention and that it may be modified in many ways within the scope of the patent claims.

The invention claimed is:

1. A laparoscopic instrument comprising:
a handle unit by which a user may hold the instrument;
an elongated third tube attached to said handle unit;
a fourth tube arranged slidable in relation to said first tube;
said fourth tube is provided with a thread gripping member capable of gripping suture threads,
a locking member arranged to said tubes such that, when said fourth tube is moved in relation to said third tube, gripped suture threads are locked;
storage means for a number of rings; and
a ring feeding member capable of, upon activation, moving said ring from said storage means to a free position in which said suture threads run through said ring, said ring feeding member comprising a second tube arranged outside said third tube.

2. The laparoscopic instrument according to claim 1, further comprising a lever member arranged adjacent to said handle and operationally connected to said fourth tube for enabling movement in relation to said third tube.

3. The laparoscopic instrument according to claim 2, wherein said storage means comprises an outer surface of said third tube, on which the rings are releasibly positioned.

4. The laparoscopic instrument according to claim 1, wherein said storage means comprises an outer surface of said third tube, on which the rings are releasibly positioned.

5. The laparoscopic instrument according to claim 1, wherein said ring feeding member further comprises a rotational member threadedly arranged to said housing and connected to said second tube such that rotation causes said second tube to be moved in the proximal direction, releasing a ring.

6. The laparoscopic instrument according to claim 1, further comprising a first tube arranged outside said second tube for protecting said ring.

7. The laparoscopic instrument according to claim 6, wherein the proximal end of said first tube is arranged with flexible arms having inwardly directed ledges at their proximal ends for releasibly holding said ring.

8. The laparoscopic instrument according to claim 1, wherein a suture thread is drawn through said fourth tube.

\* \* \* \* \*